United States Patent
Watakabe et al.

(10) Patent No.: US 8,557,474 B2
(45) Date of Patent: Oct. 15, 2013

(54) FLUOROSULFONYL GROUP-CONTAINING MONOMER AND ITS POLYMER, AND SULFONIC ACID GROUP-CONTAINING POLYMER

(75) Inventors: Atsushi Watakabe, Tokyo (JP); Hiromasa Yamamoto, Tokyo (JP); Masao Iwaya, Tokyo (JP); Susumu Saito, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 93 days.

(21) Appl. No.: 12/955,443

(22) Filed: Nov. 29, 2010

(65) Prior Publication Data

US 2011/0071272 A1 Mar. 24, 2011

Related U.S. Application Data

(63) Continuation of application No. 12/186,947, filed on Aug. 6, 2008, now abandoned.

(30) Foreign Application Priority Data

Aug. 9, 2007 (JP) ................................ 2007-208024

(51) Int. Cl.
*C08F 14/26* (2006.01)

(52) U.S. Cl.
USPC ........... 429/494; 526/243; 526/250; 526/270; 526/286; 562/103

(58) Field of Classification Search
USPC ................... 526/243, 270, 286, 255; 562/103
See application file for complete search history.

(56) References Cited

U.S. PATENT DOCUMENTS

| | | | |
|---|---|---|---|
| 7,531,610 B2 | 5/2009 | Kaneko et al. | |
| 7,667,083 B2 | 2/2010 | Kaneko et al. | |
| 7,709,665 B2 | 5/2010 | Okazoe et al. | |
| 8,124,295 B2 * | 2/2012 | Shimohira et al. | 429/492 |
| 8,394,865 B2 * | 3/2013 | Umemura et al. | 521/27 |
| 2004/0230018 A1 | 11/2004 | Okazoe et al. | |
| 2006/0099476 A1 | 5/2006 | Watakabe et al. | |
| 2006/0106252 A1 * | 5/2006 | Murata et al. | 562/825 |
| 2008/0146841 A1 | 6/2008 | Kaneko et al. | |
| 2008/0161511 A1 * | 7/2008 | Watakabe et al. | 526/79 |
| 2009/0187044 A1 | 7/2009 | Kaneko et al. | |

FOREIGN PATENT DOCUMENTS

| | | | |
|---|---|---|---|
| JP | 2005-314388 | | 11/2005 |
| JP | 2006-290864 | | 10/2006 |
| JP | 2006302600 A | * | 11/2006 |
| WO | WO 03/037885 | | 5/2003 |
| WO | WO 2007/013532 | | 2/2007 |
| WO | WO 2007013533 A1 | * | 2/2007 |

OTHER PUBLICATIONS

Carey et al., Advanced Organic Chemistry, Part B: Reactions and Synthesis, 1990, Third Edition, p. 633.*

* cited by examiner

*Primary Examiner* — Nicole M Buie-Hatcher
(74) *Attorney, Agent, or Firm* — Oblon, Spivak, McClelland, Maier & Neustadt, L.L.P.

(57) ABSTRACT

A fluorosulfonyl group-containing monomer having a high polymerization reactivity and plural fluorosulfonyl groups, a fluorosulfonyl group-containing polymer and a sulfonic acid group-containing polymer, obtained by using the monomer.

3 Claims, No Drawings

FLUOROSULFONYL GROUP-CONTAINING MONOMER AND ITS POLYMER, AND SULFONIC ACID GROUP-CONTAINING POLYMER

REFERENCE TO RELATED APPLICATION

The present application is a Continuation of U.S. application Ser. No. 12/186,947, pending, the entire contents of which are hereby incorporated by reference.

BACKGROUND OF THE INVENTION

1. Field of the Invention

The present invention relates to a fluorosulfonyl group-containing polymer which is a precursor of a sulfonic acid group-containing polymer useful as an ion-exchange membrane (e.g. a membrane to be used for brine electrolysis or polymer electrolyte fuel cells) or an electrolyte membrane to be used for a catalyst layer of a fuel cell; and a new fluorosulfonyl group-containing monomer which can be a raw material of the polymer. Further, the present invention relates to a process for producing the fluorosulfonyl group-containing monomer and a new compound useful as an intermediate for production of the monomer. Furthermore, it relates to a sulfonic acid group-containing polymer obtainable from the above fluorosulfonyl group-containing polymer and an electrolyte material for polymer electrolyte fuel cells, which comprises the sulfonic acid group-containing polymer.

2. Discussion of Background

Heretofore, a copolymer of a fluorinated monomer of the following formula and tetrafluoroethylene, has been used as a membrane for brine electrolysis, a membrane of a polymer electrolyte fuel cell or its catalyst layer. In the following formula, Y is a fluorine atom or a trifluoromethyl group, n is an integer of from 1 to 12, m is an integer of from 0 to 3, k is 0 or 1, and m+k>0:

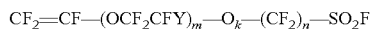

$CF_2=CF-(OCF_2CFY)_m-O_k-(CF_2)_n-SO_2F$

Further, the fluorosulfonyl group ($-SO_2F$) in the copolymer can be converted to a sulfonic acid group ($-SO_3H$) by alkali hydrolysis, followed by acid treatment.

When used for a brine electrolysis cell as a membrane having a high ion-exchange capacity, such a sulfonic acid group-containing polymer (hereinafter referred to as the sulfonic acid polymer) is a polymer which can reduce the power for the electrolysis. When the sulfonic acid polymer is used for a fuel cell, the polymer can improve the power generation energy efficiency. Further, the sulfonic acid polymer is preferably a polymer having a higher ion-exchange capacity and a lower electric resistance.

However, if the proportion of the fluorosulfonyl group-containing monomer to be used for copolymerization, is increased for a purpose of increasing the ion-exchange capacity of the sulfonic acid polymer, there has been a problem such that the molecular weight of the copolymer becomes low. A membrane formed by the copolymer having low molecular weight is insufficient in mechanical strength and durability, and thus it is not practically useful. It has been proposed to use a fluorosulfonyl group-containing monomer having plural fluorosulfonyl groups as a means to increase the ion-exchange capacity of the sulfonic acid polymer without increasing the proportion of the fluorosulfonyl group-containing monomer (Patent Document 1).

Further, in order to obtain a sulfonic acid polymer having a high molecular weight, the fluorosulfonyl group-containing monomer is required to have high copolymerizability with other fluoromonomers such as tetrafluoroethylene, but the conventional fluorosulfonyl group-containing monomer did not sufficiently have such copolymerizability. As a fluorosulfonyl group-containing monomer having a high polymerization reactivity, a perfluoro(2-methylene-1,3-dioxolane) derivative having a fluorosulfonyl group is known (Patent Documents 2, 3 and 4). However, such a derivative having plural fluorosulfonyl groups is not known.

Patent Document 1: WO2007/013532
Patent Document 2: WO03/037885
Patent Document 3: JP-A-2005-314388
Patent Document 4: JP-A-2006-290864

SUMMARY OF THE INVENTION

The present invention has an object to provide an electrolyte material for polymer electrolyte fuel cells, which is an electrolyte material having a high ion-exchange capacity and low resistance, and which has a higher softening point than a commonly used electrolyte material and is excellent in durability. Further, the present invention has an object to provide a new monomer and a polymer to prepare such a material.

The present invention provides a fluorosulfonyl group-containing monomer having a high polymerization reactivity and plural fluorosulfonyl groups. The perfluoro(2-methylene-1,3-dioxolane) derivative having two fluorosulfonyl groups of the present invention is a new monomer.

The present invention is the following invention, which relates to a fluorosulfonyl group-containing perfluoromonomer having two fluorosulfonyl groups and a high polymerization reactivity; its production process and its synthetic intermediate; a fluorosulfonyl group-containing polymer obtained by polymerizing the perfluoromonomer; a process for producing a sulfonic acid polymer from the polymer; and the sulfonic acid polymer and an electrolyte material for polymer electrolyte fuel cells, which comprises the sulfonic acid polymer.

(1) A compound represented by the following formula (3):

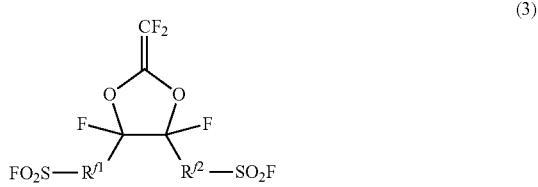

(3)

wherein each of $R^{f1}$ and $R^{f2}$ which are independent of each other, is a $C_{1-8}$ perfluoroalkylene group which may have an etheric oxygen atom between carbon atoms.

(2) The compound according to the above (1), wherein each of $-R^{f1}-SO_2F$ and $-R^{f2}-SO_2F$ is a perfluorinated 2-fluorosulfonyl ethoxy group-substituted alkylene group (the alkylene group has 1 to 3 carbon atoms).

(3) A process for producing a compound represented by the following formula (3) which comprises heat-decomposing a compound represented by the following formula (2):

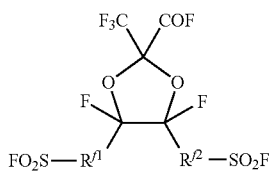
(2)

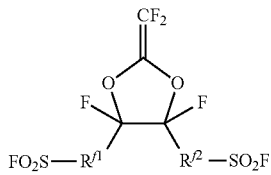
(3)

wherein each of $R^{f1}$ and $R^{f2}$ which are independent of each other, is a $C_{1-8}$ perfluoroalkylene group which may have an etheric oxygen atom between carbon atoms.

(4) The process according to the above (3), wherein each of —$R^{f1}$—$SO_2F$ and —$R^{f2}$—$SO_2F$ is a perfluorinated 2-fluorosulfonyl ethoxy group-substituted alkylene group (the alkylene group has 1 to 3 carbon atoms).

(5) The process according to the above (3) or (4), wherein the compound represented by the above formula (2) is produced from a compound represented by the following formula (1) through (a) a step of epoxidation, (b) a step of forming a dioxolane ring and (c) a step of fluorination:

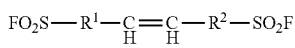
(1)

wherein each of $R^1$ and $R^2$ which are independent of each other, is a $C_{1-8}$ alkylene group which may have an etheric oxygen atom between carbon atoms and of which some or all of hydrogen atoms may be substituted by fluorine atoms.

(6) The process according to the above (5), wherein each of —$R^1$—$SO_2F$ and —$R^2$—$SO_2F$ is a 2-fluorosulfonyl-tetrafluoroethoxy group-substituted alkylene group (the alkylene group has 1 to 3 carbon atoms).

(7) A compound represented by the following formula (2):

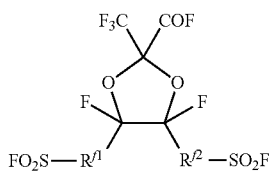
(2)

wherein each of $R^{f1}$ and $R^{f2}$ which are independent of each other, is a $C_{1-8}$ perfluoroalkylene group which may have an etheric oxygen atom between carbon atoms.

(8) The compound according to the above (7), wherein each of —$R^{f1}$—$SO_2F$ and —$R^{f2}$—$SO_2F$ is a perfluorinated 2-fluorosulfonyl ethoxy group-substituted alkylene group (the alkylene group has 1 to 3 carbon atoms).

(9) A process for producing a fluorosulfonyl group-containing polymer, which comprises polymerizing at least one compound represented by the following formula (3), or at least one such a compound and at least one polymerizable monomer copolymerizable with such a compound:

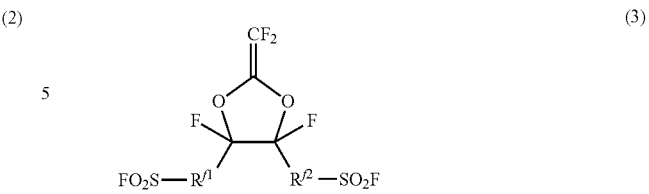
(3)

wherein each of $R^{f1}$ and $R^{f2}$ which are independent of each other, is a $C_{1-8}$ perfluoroalkylene group which may have an etheric oxygen atom between carbon atoms.

(10) A fluorosulfonyl group-containing polymer comprising at least one type of monomer units represented by the following formula (3U), or at least one type of such monomer units and at least one type of other monomer units:

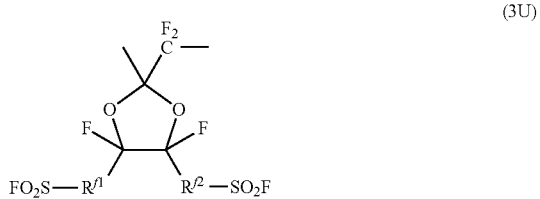
(3U)

wherein each of $R^{f1}$ and $R^{f2}$ which are independent of each other, is a $C_{1-8}1$ perfluoroalkylene group which may have an etheric oxygen atom between carbon atoms.

(11) The fluorosulfonyl group-containing polymer according to the above (10), which has a molecular weight of from $5\times10^3$ to $5\times10^6$, and which, when containing said other monomer units, contains from 0.1 to 99.9 mol % of monomer units represented by the formula (3U).

(12) A process for producing a polymer containing sulfonate groups or sulfonic acid groups, which comprises subjecting the fluorosulfonyl group in the fluorosulfonyl group-containing polymer according to the above (10) or (11) to an alkali hydrolysis, or to such an alkali hydrolysis, followed by an acid treatment.

(13) A sulfonic acid group-containing polymer containing at least one type of units represented by the following formula (5U), or at least one type of such units and at least one type of other units:

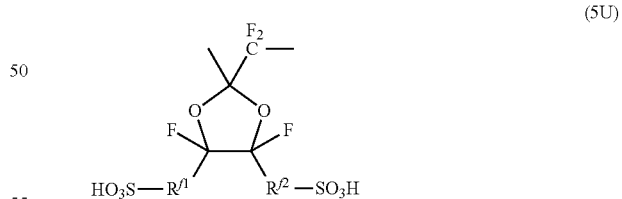
(5U)

wherein each of $R^{f1}$ and $R^{f2}$ which are independent of each other, is a $C_{1-8}$ perfluoroalkylene group which may have an etheric oxygen atom between carbon atoms.

(14) The sulfonic acid group-containing polymer according to the above (13), which has a molecular weight of from $5\times10^3$ to $5\times10^6$, and which, when containing other units, contains from 0.1 to 99.9 mol % of units represented by the formula (5U).

(15) An electrolyte material for polymer electrolyte fuel cells, which comprises the sulfonic acid group-containing polymer according to the above (13) or (14).

The monomer of the present invention is a perfluoromonomer having a perfluoro(2-methylene-1,3-dioxolane) structure having a high polymerization reactivity and two fluorosulfonyl groups, whereby it is easy to obtain a copolymer having a high molecular weight by copolymerizing it with a copolymerizable monomer such as tetrafluoroethylene, and it is easy to obtain a sulfonic acid polymer having high mechanical strength and durability. Further, since the monomer of the present invention has two fluorosulfonyl groups, it is possible to obtain a sulfonic acid polymer having a high ion-exchange capacity even if its copolymerization ratio is low, as compared with a monomer having one fluorosulfonyl group.

The sulfonic acid polymer of the present invention is useful as an electrolyte material for polymer electrolyte fuel cells since it has a low electric resistance owing to its high ion-exchange capacity; has a high softening point and excellent mechanical strength; and further has durability. Since the electrolyte material has a high softening point, it is possible to operate a cell at a higher temperature than conventional ones, and it is possible to make the fuel cell have a high output or improve the cooling efficiency.

DETAILED DESCRIPTION OF THE PREFERRED EMBODIMENTS

In the present specification, a compound represented by the formula (3) is shown as a compound (3). Further, a group represented by the formula (3a) is shown as a group (3a), and units represented by the formula (3U) are shown as units (3U). A polymer containing units (3U) is shown as a polymer (3U). The same applies to compounds, groups, units or polymers represented by other formulae.

Units in a polymer mean units derived from a monomer as formed by polymerization of the monomer, and the units in the present invention may be units directly formed from a polymerization reaction or units formed by a chemical conversion after the polymerization reaction. Among such units, the units maintaining the monomer structure except for the unsaturated groups which transform by polymerization reaction of the monomer, are referred to as monomer units.

Hereinafter, a fluorosulfonyl group may also be shown as a —SO$_2$F group, a fluorocarbonyl group as a —COF group and a sulfonic acid group as a —SO$_3$H group.

The present invention provides the following compound (3).

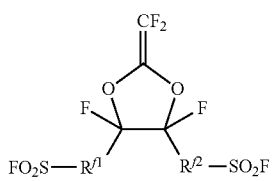

(3)

In the compound (3), each of R$^{f1}$ and R$^{f2}$ which are independent of each other, is a C$_{1-8}$ perfluoroalkylene group which may have an etheric oxygen atom between carbon atoms. Number of carbon atoms in each perfluoroalkylene group is more preferably from 1 to 6, particularly preferably from 2 to 5. Further, when the number of carbon atoms in each perfluoroalkylene group is at least 2, an etheric oxygen atom may be contained between the carbon atoms, and the number of the etheric oxygen atoms is preferably 1 or 2, particularly preferably 1. Further, each perfluoroalkylene group is preferably linear or branched to have at most two trifluoromethyl groups, particularly preferably linear. Moreover, R$^{f1}$ and R$^{f2}$ are preferably the same groups, but not so restricted. For example, R$^{f1}$ and R$^{f2}$ may be perfluoroalkylene groups different in number of carbon atoms, and may be perfluoroalkylene groups such that one has an etheric oxygen atom, and the other has no etheric oxygen atom.

Each of —R$^{f1}$—SO$_2$F and —R$^{f2}$—SO$_2$F in the compound (3) is preferably a group represented by the following formula (s-1). In the formula, p is an integer of at least 1, q is an integer of at least 1, p+q is from 2 to 5, and r is 0 or 1. The group (s-1) preferably has p of from 1 to 3, q of 2 and r of 1, namely preferably is a perfluorinated 2-fluorosulfonyl ethoxy group-substituted alkylene group (the alkylene group has 1 to 3 carbon atoms).

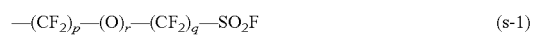

Specific examples of the compound (3) are the following compounds:

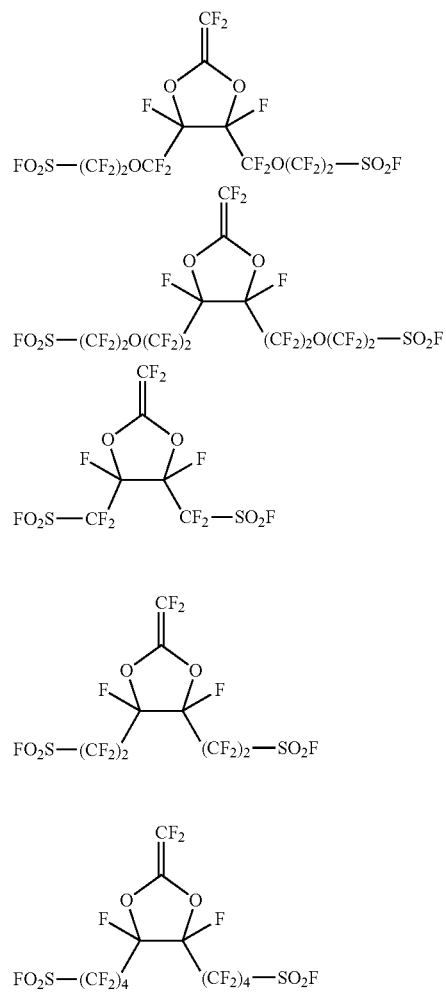

The compound (3) of the present invention can be produced by heat-decomposing the following compound (2). R$^{f1}$ and R$^{f2}$ in the compound (2) corresponding to R$^{f1}$ and R$^{f2}$ in the compound (3), are C$_{1-8}$ perfluoroalkylene groups which may have an etheric oxygen atom between carbon atoms. Further, the compound (2) is a new compound.

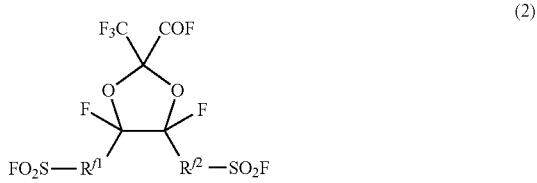

(2)

The heat-decomposition of the compound (2) may be carried out in accordance with a method described in the above Patent Document 2, 3 or 4 such that by heat-decomposing a 1,3-dioxolane derivative having a —COF group and a trifluoromethyl group at the 2-position, a 1,3-dioxolane derivative having a difluoromethylene (=CF$_2$) group at the 2-position is produced. A summary of the heat-decomposition of the compound (2) is described as follows.

The heat-decomposition reaction can be carried out by a gas phase reaction or a liquid phase reaction, and it is preferably carried out by a gas phase reaction from the viewpoint of efficiency. Further, the method for the heat-decomposition reaction and the reaction temperature are preferably selected depending on the boiling point or stability of the compound (2). Further, the compound (2) preferably has a boiling point of at most 350° C. for such a reason that the heat-decomposition reaction can thereby be carried out efficiently by a gas phase reaction. Moreover, the gas phase reaction is preferably carried out in the presence of glass beads, an alkali metal salt or an alkaline earth metal salt.

The gas phase reaction is preferably carried out by a continuous reaction. The continuous reaction is preferably carried out by a process such that a vaporized compound (2) is let flow in a heated reaction tube, and a formed compound (3) is obtained as an outlet gas, followed by condensation to recover it continuously. When the heat-decomposition is carried out by a gas phase reaction, the reaction temperature is preferably at least 150° C., particularly preferably from 200° C. to 500° C., especially preferably from 250° C. to 450° C. If the reaction temperature is too high, the yield tends to be low by a decomposition reaction of the product. Further, when the heat-decomposition reaction is carried out by a gas phase reaction, it is preferred to use a tube-type reactor. When the tube-type reactor is used, the retention time is preferably approximately from 0.1 second to 10 minutes based on a void tower standard. The reaction pressure is not particularly limited.

When the gas phase reaction is carried out by using the tube-type reactor, the reaction tube is preferably packed with glass, an alkali metal salt or an alkaline earth metal salt, for a purpose of accelerating the reaction. The alkali metal salt or the alkaline earth metal salt is preferably a carbonate or a fluoride. The glass may be common soda glass, and particularly preferably glass bead having increased mobility.

With respect to the gas phase reaction, for a purpose of accelerating the vaporization of the compound (2), the reaction is preferably carried out in the presence of an inert gas which does not get directly involved in the heat-decomposition reaction. The inert gas may, for example, be nitrogen, carbon dioxide, helium or argon. The concentration of the compound (2) in the inert gas is preferably approximately from 0.01 to 50 vol %.

The heat-decomposition reaction can also be carried out after the compound (2) is converted to alkali metal or alkaline earth metal salt of the corresponding carboxylic acid. In such a method, the compound (2) is led to alkali metal or alkaline earth metal salt of the corresponding carboxylic acid in the presence of a solvent, by a reaction with a carbonate or a hydrogen carbonate of alkali metal or alkaline earth metal, followed by removal of the solvent. In such a method, it is possible to selectively lead a —COF group to a salt of carboxylic acid without hydrolyzing a —SO$_2$F group in the compound (2). The solvent may be a nonpolar solvent or a polar solvent, and it is preferably a polar solvent since the reaction can thereby be carried out at a low temperature. The heat-decomposition temperature of an alkali metal salt of the compound (2) is preferably from 100 to 300° C., particularly preferably from 150 to 250° C. The heat-decomposition reaction via an alkali metal salt is preferred since it can be carried out at a low temperature as compared with a heat-decomposition method in a gas phase.

The compound (2) can be produced in accordance with a method described in the above Patent Document 2, 3 or 4. Such documents describe a process for producing a 1,3-dioxolane derivative (having one —SO$_2$F group) having a —COF group and a trifluoromethyl group at the 2-position from a starting material of a monoene having one —SO$_2$F group via a step of epoxidation and a step of forming a 1,3-dioxolane ring. Further, in a case where the 1,3-dioxolane derivative obtained in the above step of forming a 1,3-dioxolane ring, has hydrogen atoms, the derivative is subsequently fluorinated to obtain a perfluorinated 1,3-dioxolane derivative which is then converted to a 1,3-dioxolane derivative (having one —SO$_2$F group) having a —COF group and a trifluoromethyl group at the 2-position. In the present invention, the compound (2) can be produced in the same manner from a starting material of a monoene having two —SO$_2$F groups.

The compound (2) is preferably produced from the compound (1) represented by the following formula via (a) a step of epoxidation, (b) a step of forming a dioxolane ring and (c) a step of fluorination. Now, such preferred process steps will be described. However, a process for producing the compound (2) is by no means restricted thereto. For example, a starting material of a perfluorinated compound corresponding to the compound (a compound wherein all hydrogen atoms in the compound (1) are fluorine atoms) may be converted to a diketone through an epoxidation of an unsaturated group portion, followed by a reaction with hexafluoropropylene oxide to obtain a 1,4-dioxane ring compound in accordance with a method disclosed in Patent Document 4. It is possible to produce the compound (2) by heat-decomposing the obtained 1,4-dioxane ring compound. Such a process does not require a step of fluorination.

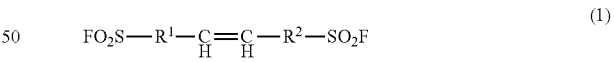

(1)

In the above formula (1), each of R$^1$ and R$^2$ which are independent of each other, is a C$_{1-8}$1 alkylene group which may have an etheric oxygen atom between carbon atoms and of which some or all of hydrogen atoms may be substituted by fluorine atoms. Further, the compound (1) may be a transform or a cis-form. Each of such R$^1$ and R$^2$ is a group corresponding to the above R$^{f1}$ or R$^{f2}$, namely, it is the same group as the above R$^{f1}$ or R$^{f2}$, or a group to be converted to the above R$^{f1}$ or R$^{f2}$ by fluorination. In the latter case, it is preferably a group having the same structure as the above R$^{f1}$ or R$^{f2}$ except that some or all of fluorine atoms in the above R$^{f1}$ or R$^{f2}$ are substituted by hydrogen atoms, and particularly preferably a group having both hydrogen atoms and fluorine atoms. The proportion of the number of the hydrogen atoms based on the total of hydrogen atoms and fluorine atoms in each of R$^1$ and $R^2$ is from 30 to 100%, particularly preferably from 30 to 70%. Further, since $R^1$ and $R^2$ are groups corresponding to the above $R^{f1}$ and $R^{f2}$, the preferred number of carbon atoms, number of etheric oxygen atoms or structure such as a linear structure, of $R^1$ and $R^2$ are the same as the above $R^{f1}$ and $R^{f2}$.

Each of —$R^1$—$SO_2F$ and —$R^2$—$SO_2F$ in the compound (1) is preferably a group represented by the following formula (s-2). In the following formula (s-2), X represents a hydrogen atom or a fluorine atom, and each X in the formula may be different. Since $R^1$ and $R^2$ are groups corresponding to the above $R^{f1}$ and $R^{f2}$, p, q and r are the same as the above group (s-1). The more preferred group represented by the following formula (s-2) is a 2-fluorosulfonyl ethoxy group-substituted alkylene group represented by the following formula (s-3) (in the formula (s-3), p is from 1 to 3).

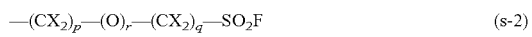
(s-2)

(s-3)

An embodiment of scheme for producing the compound (2) from the compound (1) represented by the following formula via (a) a step of epoxidation, (b) a step of forming a dioxolane ring and (c) a step of fluorination, is shown as follows. Here, the following compound (1) may be a cis-form or a trans-form, and the compound (1) used in Examples given hereinafter was a trans-form.

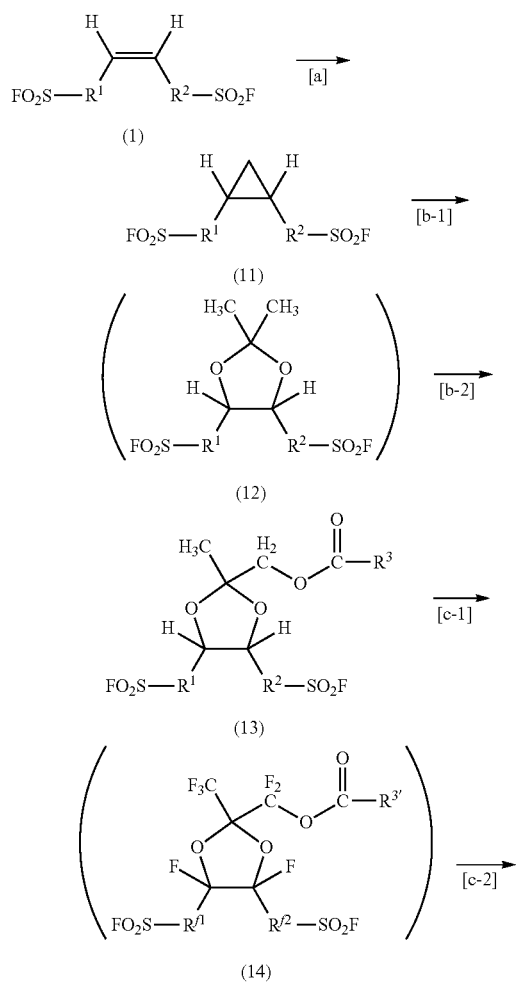

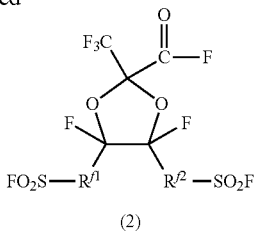
(2)

In the above formula (13), $R^3$ represents an alkyl group or a polyfluoroalkyl group which may contain an etheric oxygen atom between carbon atoms. The number of carbon atoms in $R^3$ is properly from 1 to 20, preferably 3 to 12. $R^3$ is particularly preferably a $C_{3-10}$ perfluoroalkyl group or an etheric oxygen atom-containing perfluoroalkyl group having 3 to 12 carbon atoms and 1 to 3 etheric oxygen atoms. $R^{3'}$ in the above formula (14) is a group (a perfluorinated group) of which the hydrogen atoms are all substituted by fluorine atoms, provided that when $R^3$ is a group containing hydrogen atoms, or the same group as $R^3$ when $R^3$ is a group (a perfluorinated group) not containing hydrogen atoms. As $R^3$ (the same for $R^{3'}$), the following perfluorinated group is particularly preferred:

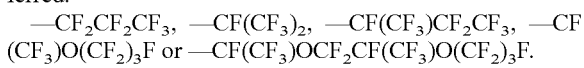

(a) A step of epoxidation in the present invention is a step of producing a compound (11) from the compound (1) in the above scheme, and it includes an epoxidation reaction [a]. (b) A step of forming a dioxolane ring is a step of producing a compound (13) from the compound (11) in the above scheme, and it includes a reaction [b-1] of forming a dioxolane ring. The compound (13) is preferably produced by a reaction [b-2] of converting a side chain group via a compound (12), but it may be produced directly from the compound (11). The reaction [b-2] of converting a side chain group is preferably a ketal exchange reaction. It is preferred to produce the compound (13) from the compound (11) by carrying out the reaction [b-1] and the reaction [b-2] without isolating the compound (12). (c) A step of fluorination is a step of producing the compound (2) from the compound (13) in the above scheme, and it includes a fluorination reaction [c-1]. The compound (2) is preferably produced by an ester-decomposition reaction [c-2] via a compound (14), but the compound (2) may sometimes be obtained from the compound (13) when the ester-decomposition reaction [c-2] proceeds simultaneously with the fluorination reaction [c-1]. It is preferred to carry out the fluorination reaction [c-1] and the ester-decomposition reaction [c-2] separately.

In (a) a step of epoxidation, the compound (11) is obtained by oxidizing the compound (1) with an oxidizing agent. As the oxidizing agent, it is possible to use oxygen gas, a hypochlorite or a peroxide. The peroxide may, for example, be m-chloroperbenzoic acid, perbenzoic acid, peracetic acid or hydrogen peroxide. The epoxidation of an unsaturated group by using such an oxidizing agent may be carried out by a known method.

In (b) a step of forming a dioxolane ring, the compound (12) is synthesized by reacting the compound (11) with acetone. At that time, instead of directly reacting the compound (11) with acetone, it is possible to react water with the compound (11) to obtain a diol, and then react such a diol with acetone to synthesize the compound (12). Such a reaction is preferably carried out in the presence of an acid catalyst. The acid catalyst may, for example, be an inorganic acid, a Lewis acid or a solid acid. Then, the compound (12) is reacted (reaction [b-2]) with hydroxyacetone ester represented by the following formula (15) to produce the compound (13). The reaction [b-2] is a ketal exchange reaction, wherein an acetone residue is converted to a hydroxyacetone ester (15) residue. Further, the compound (13) may also be produced in such a manner that the compound (12) is subjected to a ketal exchange reaction with a hydroxyacetone to convert an acetone residue to a hydroxyacetone residue, and then its hydroxyl group is converted to a R³COO— group. With respect to such a ketal exchange reaction, it is preferably carried out, in the presence of the above acid catalyst, by removing acetone which forms as a byproduct in a high boiling point solvent, from the reaction system. Further, it is possible to sequentially carry out the reaction [b-1] and reaction [b-2] by changing the reaction condition while the compound (11), acetone and the compound (15) are permitted to coexist. Further, it is also possible to obtain the compound (13) by reacting the compound (11) or its diol compound with hydroxyacetone ester (15).

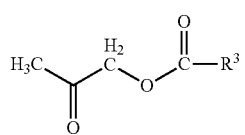

(15)

In (c) a step of fluorination, first, all hydrogen atoms in the compound (13) are substituted by fluorine atoms by a fluorination reaction [c-1] to obtain the compound (14). A method for the fluorination reaction may, for example, be a method for a reaction with fluorine in a gas phase, or a method for a fluorination reaction carried out in a liquid phase such as an electro-chemical fluorination method (ECF method) or a cobalt fluorination method. From the viewpoint of handling efficiency and the yield of the reaction, the fluorination carried out in a liquid phase is a particularly advantageous method, and a method of reacting the compound (13) with fluorine (F₂) in a liquid phase (namely, a method so-called a liquid phase fluorination) is particularly preferred. Details of the liquid phase fluorination are described not only in the above Patent Document 2, but also in WO00/056694, etc.

In the liquid phase fluorination, as fluorine, it is possible to use fluorine gas as it is or fluorine gas diluted by an inert gas such as nitrogen gas. The amount of fluorine in an inert gas is preferably at least 10 vol %, particularly preferably at least 20 vol %.

In the liquid phase fluorination, a solvent is usually used in order to form a liquid phase. The solvent is preferably a solvent which does not contain a C—H bond and essentially contains a C—F bond, or a fluorinated solvent having at least one atom selected from a group consisting of a chlorine atom, a nitrogen atom or an oxygen atom, in the structure and containing no C—H bond (hereinafter such a fluorine type solvent including a perfluoroalkane is referred to as a perfluoro-solvent). The solvent may be a solvent inactive in the fluorination reaction, and it may have a functional group active in other reactions. For example, it is possible to use, as a solvent, a perfluoroether or a perfluoroalkane having a fluorocarbonyl group (—COF group). Further, as the solvent, it is preferred to use a solvent presenting a high solubility for the compound (13). Especially, it is preferred to use a solvent which can dissolve at least 1 mass % of the compound (13), particularly preferred to use a solvent which can dissolve at least 5 mass %. Further, the amount of the solvent is preferably at least 5 times by mass, particularly preferably from 10 to 100 times by mass, based on the compound (13).

The reaction style of the liquid phase fluorination reaction may be a batch system or a continuous system. Particularly, it is preferred to carry out the fluorination in such a manner that a solvent is charged in a reactor, and stirring is started, and after the reaction temperature and the reaction pressure are controlled at prescribed levels, the fluorine gas and the compound (13) are continuously and simultaneously supplied in a prescribed molar ratio.

The amount of fluorine to be used for the liquid phase fluorination is preferably constantly in excess by equivalent relative to hydrogen atoms to be fluorinated, particularly preferably at least 1.5 times by equivalent (namely, at least 1.5 mol) from the viewpoint of selectivity, when the reaction is carried out either by a batch system or a continuous system. Further, the amount of fluorine is preferably kept to be constantly in excess by equivalent from the beginning of the reaction to the end of the reaction.

The reaction temperature for the liquid phase fluorination is usually preferably at least −60° C. and at most the boiling point of the compound (13), particularly preferably from −50° C. to +100° C. from the viewpoint of the reaction yield, selectivity and industrial operation efficiency, particularly preferably from −20° C. to +50° C. The reaction pressure for the liquid phase fluorination is not particularly limited, and it is particularly preferably from a normal pressure to 2 MPa from the viewpoint of the reaction yield, selectivity and industrial operation efficiency.

Further, in order to let the liquid phase fluorination efficiently proceed, it is preferred to add a C—H bond-containing compound in the reaction system at a late stage of the reaction or to carry out ultraviolet irradiation. By using the C—H bond-containing compound, it is possible to efficiently fluorinate the compound (13) present in the reaction system, and it is possible to improve the reaction rate significantly. The C—H bond-containing compound is an organic compound other than the compound (13), and specifically, it is preferably an aromatic hydrocarbon, particularly preferably benzene or toluene. The amount of the C—H bond-containing compound to be added is preferably from 0.1 to 10 mol %, particularly preferably from 0.1 to 5 mol %, based on hydrogen atoms in the compound (13).

HF which forms as a byproduct in the liquid phase fluorination is removed by an HF capture agent such as NaF, and the product and the solvent are separated to obtain the compound (14) as a product. The compound (14) obtained by the fluorination may be subjected to an ester-decomposition reaction [c-2] as it is in the form of a crude product, or may be subjected to an ester-decomposition reaction [c-2] after purification.

The ester-decomposition reaction [c-2] of the compound (14) is preferably carried out by a decomposition reaction by heat or a decomposition reaction to be carried out in a liquid phase in the presence of a nucleophilic agent or an electrophile.

The decomposition reaction by heat can be carried out by heating the compound (14). The reaction temperature of the gas phase heat-decomposition reaction is preferably from 50 to 350° C., particularly preferably from 50 to 300° C., particularly preferably from 150 to 250° C. Further, it is permitted to let coexist an inert gas such as nitrogen which does not get directly involved with the reaction, in the reaction system. It is preferred to add the inert gas approximately from 0.01 to 50 vol % based on the compound (14). If the amount of the inert gas to be added is large, the recovered amount of the product may sometimes be lowered.

It is also possible to use a liquid phase heat-decomposition reaction which heats up the compound (14) in a liquid state in the reactor. In such a case, the reaction pressure is not limited. In a usual case, since the product containing the compound (2) has a lower boiling point than the compound (14), the product is preferably obtained by a method of a reaction distillation system wherein the product is vaporized and continuously withdrawn. Further, it may be obtained by a method wherein after the completion of heating, the product is withdrawn from the reactor all at once. The reaction temperature of such a liquid phase heat-decomposition reaction is preferably from 50 to 300° C., particularly preferably from 100 to 250° C.

The liquid phase heat-decomposition reaction may be carried out in the presence or absence of a solvent. The solvent is not particularly limited as long as it is one which does not react with the compound (14), has a compatibility with the compound (14) and does not react with the compound (2) to be formed. Further, as the solvent, it is preferred to select one easily separable at the time of purification of the compound (2). Specific examples of the solvent may be a perfluorinated solvent such as perfluorotrialkylamine or perfluorodecaline, and a fluorinated inactive solvent such as chlorotrifluoroethylene oligomer. Further, the amount of the solvent is preferably from 10 to 1,000 mass % based on the compound (14).

Further, the compound (14) can be subjected to an ester-decomposition by a reaction with a nucleophilic agent or an electrophile in a liquid phase in the absence of a solvent or in the presence of the above fluorinated inactive solvent. Particularly, it is preferred that the compound is subjected to the ester-decomposition by a reaction with the nucleophilic agent. The nucleophilic agent is preferably $F^-$, particularly preferably $F^-$ derived from a fluoride of an alkali metal. The fluoride of an alkali metal is preferably NaF, $NaHF_2$, KF or CsF. Among them, NaF is particularly preferred from the viewpoint of economic efficiency, and KF is particularly preferred from the viewpoint that the reaction can be carried out at a low reaction temperature. When the nucleophilic agent (e.g. $F^-$) is used, the nucleophilic agent used at the beginning of the reaction may be in a catalytic amount and may be used excessively. That is, the amount of the nucleophilic agent such as $F^-$ is preferably from 1 to 500 mol %, particularly preferably from 1 to 100 mol %, especially preferably from 5 to 50 mol %, based on the compound (14). The reaction temperature is preferably from −30° C. to the boiling point of the solvent or the compound (14), particularly preferably from −20° C. to 250° C. This method is also preferably carried out by a reaction distillation system.

The compound (1) as a starting material in the above process can be produced by a known method or in accordance with a known method. For example, in the above Patent Document 2, it is disclosed that an alkenyl compound having a $-SO_2F$ group is obtained by reacting a bromoalkene with tetrafluoroethane-1,2-sultone (hereinafter referred to simply as sultone). Accordingly, it is possible to obtain a compound (1) as an unsaturated compound having two $-SO_2F$ groups by reacting dibromoalkene with sultone. Further, the above Patent Document 3 discloses a process to obtain an alkenyl compound having a $-SO_2F$ group from an alkenyl alcohol via an alkenyl compound having a $-SO_2(OZ)$ group (Z: alkali metal). Accordingly, it is possible to obtain a compound (1) as an unsaturated compound having two $-SO_2F$ groups from an alkenediol via an unsaturated compound having two $-SO_2(OZ)$ groups (Z: alkali metal). A specific example of such a method may be a method to obtain a compound (1) having a group (s-3) represented by the following formula (1a) by a reaction of a compound represented by the following formula (10a) with sultone represented by the formula (10b). Further, as mentioned above, the compound (10a) or the compound (1a) may be a cis-form or a trans-form, and in the Examples given hereinafter, the trans-form is used.

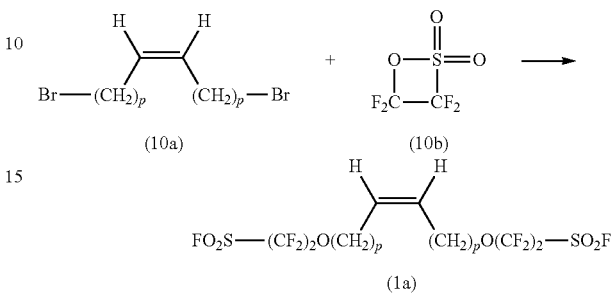

The present invention is a fluorosulfonyl group-containing polymer comprising at least one type of monomer units represented by the following formula (3U) or at least one type of such monomer units and at least one type of other monomer units. The monomer units (3U) are monomer units formed by polymerization of the compound (3). $R^{f1}$ and $R^{f2}$ in the monomer unit (3U) are the same as $R^{f1}$ and $R^{f2}$ in the compound (3).

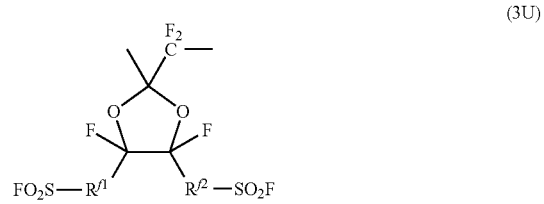

The polymer having the monomer units (3U) (namely, a polymer (3U)) is useful as a precursor of an electrolyte material to be used for an application to a brine electrolysis or a fuel cell. For example, a fluorosulfonyl group-containing polymer as a homopolymer or copolymer of the compound (3) is useful as a precursor of a sulfonic acid polymer having a high molecular weight and a high ion-exchange capacity. Such a copolymer may be obtained by copolymerizing the compound (3) with another polymerizable monomer (hereinafter referred to as a comonomer) copolymerizable with the compound (3). The comonomer may be one type or at least two types.

The comonomer may, for example, be a perfluoromonomer such as tetrafluoroethylene, a perfluoro(α-olefin) such as hexafluoropropene, a perfluorodiene such as perfluoro(3-butenyl vinyl ether), perfluoro(alkyl vinyl ether) or perfluoro (3,5-dioxa-1,6-heptadiene), a perfluorinated cyclic monomer such as perfluoro(2,2-dimethyl-1,3-dioxole), perfluoro(1,3-dioxole), perfluoro(2-methylene-4-methyl-1,3-dioxolane) or perfluoro(4-methoxy-1,3-dioxole), or perfluorovinyl ether such as perfluoro(alkyl vinyl ether) or perfluoro(alkoxyalkyl vinyl ether).

Further, as the comonomer, it is possible to use a comonomer other than a perfluoromonomer, which may be copolymerized with the compound (3) alone or may be copolymerized with the compound (3) together with the above exemplified comonomer. Specifically, such a comonomer may, for example, be a fluoroolefin such as trifluoroethylene, chlorotrifluoroethylene, vinylidene fluoride or vinyl fluoride, an olefin such as ethylene or propene, a (perfluoroalkyl)ethylene such as (perfluorobutyl)ethylene, or a (perfluoroalkyl) propene such as 3-perfluorooctyl-1-propene. Further, it is possible to use, as a comonomer, a monomer having a —$SO_2F$ group other than the compound (3), particularly a perfluorinated monomer having a —$SO_2F$ group.

The polymerization reaction is not particularly limited as long as it is carried out under such a condition that radicals are produced. For example, it may be carried out by bulk polymerization, solution polymerization, suspension polymerization, emulsion polymerization, or polymerization in a liquid or supercritical carbon dioxide.

A method for producing radicals is not particularly limited. For example, it is possible to use a method of irradiating radioactive rays such as ultraviolet rays, γ-rays or electron rays, and it is also possible to use a method of using a radical initiator usually used in radical polymerization. The reaction temperature for the polymerization reaction is not particularly limited, and for example, it is usually from 15 to 150° C. In a case where a radical initiator is used, the radical initiator may, for example, be a bis(fluoroacyl)peroxide, a bis(chlorofluoroacyl)peroxide, a dialkyl peroxy carbonate, a diacyl peroxide, a peroxyester, an azo compound or a persulfate.

When solution polymerization is to be carried out, a solvent to be used usually preferably has a boiling point of from 20 to 350° C., more preferably from 40 to 150° C. from the viewpoint of handling efficiency. As the solvent, a solvent is used wherein growing radicals for the polymerization will cause no or little chain transfer reaction to the solvent. Such a solvent is preferably a fluorinated solvent which is usually used for polymerization of a fluorinated monomer. For example, it may be a hydrofluorocarbon, a hydrochlorofluorocarbon, a chlorofluorocarbon, a perfluorocarbon, a polyfluorodialkyl ether, a polyfluorinated cyclic ether or a polyfluorotrialkylamine.

Further, it is possible to carry out polymerization by using a chain transfer agent to adjust the molecular weight. The chain transfer agent may, for example, be an alcohol such as methanol or ethanol, the above fluorinated solvent such as a hydrochlorofluorocarbon which functions also as a chain transfer agent, or a hydrocarbon such as pentane, hexane or cyclohexane.

The molecular weight of the polymer (3U) (namely, a homopolymer or copolymer having monomer units (3U)) is preferably from $5 \times 10^3$ to $5 \times 10^6$, particularly preferably from $1 \times 10^4$ to $3 \times 10^6$. When comonomer units are contained, it is preferred to contain the monomer units (3U) in a proportion of from 0.1 to 99.9 mol % based on the total of monomer units. The proportion of the monomer units (3U) is particularly preferably from 5 to 90 mol %, especially preferably from 10 to 75 mol %.

The copolymer in the polymer (3U) is particularly useful for an application to a precursor of an electrolyte material for a brine electrolysis or a fuel cell. Further, when the copolymer is used for an application to a brine electrolysis or a fuel cell, the comonomer is preferably selected from perfluorinated comonomers from the viewpoint of durability. The comonomer is preferably a perfluoroolefin such as tetrafluoroethylene or a perfluoro(alkyl vinyl ether), especially preferably a tetrafluoroethylene.

A sulfonic acid polymer useful as an electrolyte material for a brine electrolysis or a fuel cell, can be produced by subjecting a fluorosulfonyl group of a polymer (3U) to alkali hydrolysis, or acid-treatment after such alkali hydrolysis. The sulfonic acid polymer to be obtained is a polymer containing units represented by the following formula (4U). However, the sulfonic acid polymer to be obtained may contain units wherein only one —$SO_2F$ group of the monomer unit (3U) is converted to a —$SO_3M$ group, or it may contain a small amount of unreacted monomer unit (3U). M in the following formula (4U) represents a hydrogen atom or a counter ion. Further, a polymer having the following units (4U) will be referred to also as a polymer (4U).

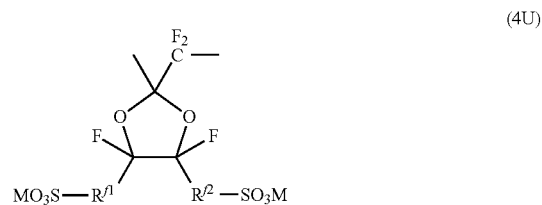

(4U)

The molecular weight of the polymer (4U) (namely, a homopolymer or a copolymer having units (4U)) is preferably from $5 \times 10^3$ to $5 \times 10^6$, particularly preferably from $1 \times 10^4$ to $3 \times 10^6$. When the comonomer units are contained, the units (4U) are preferably contained in a proportion of 0.1 to 99.9 mol % based on the total monomer units. The proportion of the units (4U) is particularly preferably from 5 to 90 mol %, especially preferably from 10 to 75 mol %.

In alkali hydrolysis of the polymer (3U), it is preferred to use an alkali metal hydroxide or an alkali metal carbonate. It is also possible to use a compound represented by a formula $NR^1R^2R^3R^4$(OH) (wherein each of $R^1$ to $R^4$ which are independent of each other, is a hydrogen atom or a $C_{1-5}$ alkyl group). In acid-treatment, it is preferred to use hydrochloric acid, nitric acid or sulfuric acid. Consequently, a fluorosulfonyl group can be converted to a sulfonate (—$SO_3M^1$ group: wherein $M^1$ represents a counter ion). Here, $M^1$ is preferably an alkali metal ion or a $N^+R^1R^2R^3R^4$. The alkali metal ion is preferably a sodium ion, a potassium ion or a lithium ion. Further, $N^+R^1R^2R^3R^4$ is preferably $N^+(CH_3)_4$, $N^+(CH_2CH_3)_4$, $N^+(CH_2CH_2CH_3)_4$ or $N^+(CH_2CH_2CH_3)_4$.

It is preferred to obtain a polymer wherein $M^1$ in the sulfonate group is an alkali metal ion, by reacting a sulfonic acid group-containing polymer with an alkali metal hydroxide. Further, it is preferred to obtain a polymer wherein $M^1$ in the sulfonate group is $N^+R^1R^2R^3R^4$, by reacting a fluorosulfonyl group-containing polymer with a compound represented by the formula $NR^1R^2R^3R^4$(OH). Further, the sulfonate group-containing polymer obtained by hydrolysis can be converted to have other counter ions by immersing the polymer in an aqueous solution containing ions which can be counter ions different from $M^1$. Further, the sulfonate group (—$SO_3M^1$ group) can be converted to a sulfonic acid group (—$SO_3H$ group) by treatment with an acid such as hydrochloric acid, nitric acid or sulfuric acid. A method for converting such groups may be carried out in accordance with a known method and conditions.

The present invention is a sulfonic acid group-containing polymer containing at least one type of units represented by the following formula (5U) or at least one type of such units and at least one type of other units. Each of $R^{f1}$ and $R^{f2}$ in the following formula (5U) is the same as the above perfluoroalkylene group. Such a polymer (5U) has its molecular weight of from $5 \times 10^3$ to $5 \times 10^6$, and when other units are contained, units represented by the formula (5U) are preferably contained in an amount of from 0.1 to 99.9 mol %.

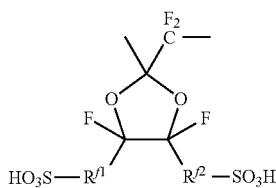
(5U)

The sulfonic acid group-containing polymer (5U) is particularly suitable as an electrolyte material for a polymer electrolyte fuel cell.

The polymer (3U) of the present invention is excellent in adhesion with other substrates. Further, it has a low refractive index as compared with a hydrocarbon type polymer, and it has a high refractive index as compared with a perfluoropolymer having no functional groups, whereby it is also useful as an optical material. Further, the polymer (4U) or the polymer (5U) obtainable by the process of the present invention are not limited in their application to an electrolyte material for a brine electrolysis or a fuel cell, and it is possible to use them for various applications as solid electrolyte materials. For example, such polymers may be used for a proton permselective membrane to be used for water electrolysis, hydrogen peroxide production, ozone production or waste acid recovery, or may be used for a cation exchange membrane for electrodialysis to be used for desalination or salt production. Further, they may also be used for a polymer electrolyte for a lithium ion cell, a solid acid catalyst, a cation exchange resin, a sensor using modified electrodes, an ion exchange filter for removing a trace amount of ions in an air, or an actuator. That is, the polymer (4U) may be used as a material for various electrochemical processes. Further, the polymer (4U) may be used for a membrane for diffusion dialysis to be used for separation and purification of an acid, a base or a salt, a charged porous membrane for protein separation (e.g. a charged reverse osmosis membrane, a charged ultrafiltration membrane or a charged microfiltration membrane), a dehumidifying membrane or a humidifying membrane.

EXAMPLES

Now, the present invention will be described in further detail with reference to Examples, but it should be understood that the present invention is by no means restricted thereto. The compounds and the reaction conditions used for a reaction scheme described in each Example are shown. Further, abbreviations described in each Example are the following.

GC: Gas chromatograph
GPC: Gel permeation chromatograph
HCFC 225: Fluorinated solvent. A mixture of $CF_3CF_2CHCl_2/CClF_2CF_2CHClF=45/55$ (mass ratio).
HCFC 225cb: Fluorinated solvent. $CClF_2CF_2CHClF$.
R 113: Fluorinated solvent. $CCl_2FCClF_2$.
$BF_3 \cdot OEt_2$: Boron trifluoride ether complex Example 1

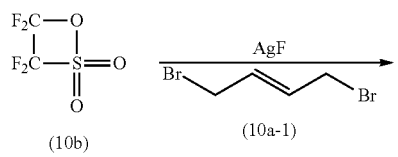

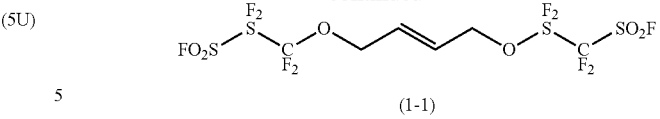
(1-1)

A 5 L 4-necked flask was equipped with a thermometer, a Dimroth condenser and a stirrer. Under an atmosphere of nitrogen, 1,800 ml of diglyme was added. Then, AgF (593 g, 4.68 mol) was added with stirring. A reactor was equipped with a dropping funnel, and the reactor was cooled in an ice bath until its inner temperature became at most 10° C. While maintaining the inner temperature of at most 10° C., sultone (10b) (843 g, 4.68 mol) was dropped from a dropping funnel over a period of 2 hours, followed by stirring for 1 hour in a water bath.

Again, the reactor was cooled in an ice bath, and while maintaining the inner temperature of at most 10° C., trans-1,3-dibromo-2-butene (10a-1) (500 g, 2.34 mol) dissolved in 500 g of diglyme was dropped from a dropping funnel over a period of 1.5 hours. After the dropping, stirring was continuously carried out for 11 hours. When the crude liquid of the reaction was subjected to a GC analysis, it was confirmed that the reaction was almost finished.

The crude liquid of the reaction was subjected to suction filtration by using celite. The filtrate was transferred to a 5 L 4-necked flask, and under a reduced pressure, the solvent was distilled off by heating. 1,067 g of the content remained in the flask. 3,200 g of deionized water was added thereto, followed by stirring for 15 minutes for water-washing treatment. 863 g (GC: 73.66%) of the lower layer was recovered by a separating funnel. After the filtration with sea sand, the recovered liquid was dried with magnesium sulfate.

500 g of a compound (1-1) was obtained by distillation. The boiling point 137 to 140° C./0.27 to 0.40 kPa. Yield 47%.

$^1$H-NMR (300.4 MHz, solvent: $CDCl_3$) δ (ppm): 6.0 (m, 2H), 4.7 (m, 4H).

$^{19}$F-NMR (282.7 MHz, solvent: $CDCl_3$, standard: $CFCl_3$) δ (ppm): 43.6 (2F), −84.1 (4F), −111.5 (4F).

Example 2

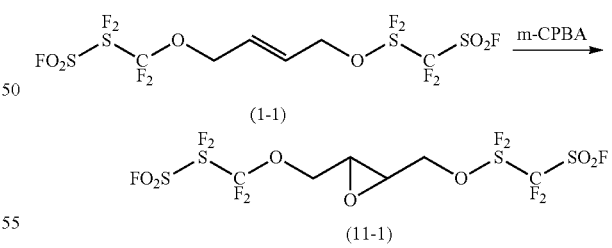

A 5 L 4-necked flask was equipped with a thermometer, a Dimroth condenser and a stirrer. Under an atmosphere of nitrogen, the compound (1-1) (475 g, 1.05 mol), 2,800 g of 1,2-dichloroethane and 352 g of m-chloroperbenzoic acid (m-CPBA) (purity >65%) were added, and reflux was carried out for 7 hours. When the mixture was subjected to a GC analysis, the degree of conversion was 36.4%. 1,029 g of 1,2-dichloroethane and 352 g of m-CPBA (purity >65%) were further added into a reactor, and reflux was carried out for 31 hours. The degree of conversion was 94.6%.

The crude liquid of the reaction was filtrated to recover 5,132 g. It was washed twice with a saturated sodium carbonate aqueous solution and with 4.8 mol/l of a sodium chloride aqueous solution, and it was subjected to liquid separation to obtain 4,859 g of a crude liquid of the reaction.

Such a crude liquid was dried over sodium sulfate and filtrated, and then it was concentrated by an evaporator and dried to obtain 400 g of a compound (11-1).

$^1$H-NMR (300.4 MHz, solvent: $CDCl_3$) δ (ppm): 4.3 (m, 2H), 4.2 (m, 2H), 2.2 (m), 3.3 (m, 2H).

$^{19}$F-NMR (282.7 MHz, solvent: $CDCl_3$, standard: $CFCl_3$) δ (ppm): 43.6 (2F), −84.3 (4F), −111.5 (4F).

Example 3

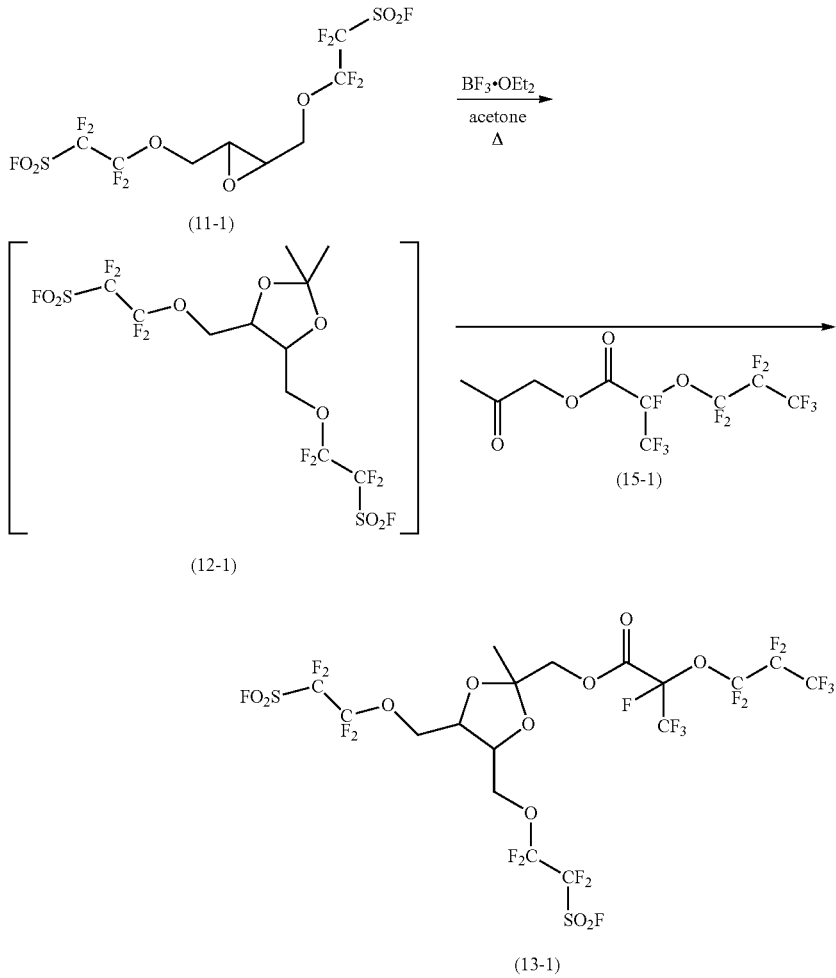

Acetonide Formation

A 1 L 4-necked flask was equipped with a thermometer, a stirrer and a Dean-Stark trap. Under an atmosphere of nitrogen, 71.32 g (152.3 mmol) of the compound (11-1), 263 g of dried acetone, 290 g of dried toluene, 58.77 g (152.2 mmol) of a compound (15-1) and $BF_3.OEt_2$ (2.67 g, 18.8 mmol) were sequentially added.

The reactor was heated in an oil bath and heated to the inner temperature of 90° C. under a normal pressure to distill 300 ml of the solvent. Then, stirring was carried out for 4 hours at the inner temperature of 100° C. The degree of conversion analyzed by gas chromatograph was 97%.

Ketal Exchange

The Dean-Stark trap was removed from the flask and a simple distillation device was attached thereto. It was heated to the inner temperature of 90° C. at 33 kPa to distill 239 g of toluene. Into the reactor, $BF_3.OEt_2$ (1.33 g, 9.37 mmol) was added, and a reaction was carried out at 40 kPa at the inner temperature of 90° C. for 2.5 hours. Further, into the reactor, $BF_3.OEt_2$ (1.39 g, 9.79 mmol) was added, and a reaction was carried out at 40 kPa at the inner temperature of 90° C. for 2 hours to obtain 141.82 g of a reaction crude liquid of a compound (13-1). The degree of conversion was 96.4%.

In the same manner, 822.6 g (degree of conversion: 93.9%) of the reaction crude liquid of the compound (13-1) was obtained from 328.24 g (701 mmol) of the compound (11-1).

Two of the above reaction crude liquid were combined and heated to the inner temperature of 100° C. at 40 kPa. Then, the pressure was gradually decreased to 0.13 kPa. After that, when the content became bubbly at the inner temperature of 107° C. by heating, the operation to distill off low-boiling components was stopped. The content in the flask was 709 g.

A silica gel ("silica gel 60", spherical shape, supplied by Kanto Chemical Co., Inc.) was used for a stationary phase, and hexane and HCFC 225 were used for a mobile phase to carry out column purification, whereby 343.7 g of the compound (13-1) was obtained.

$^1$H-NMR (300.4 MHz, solvent: CDCl$_3$) δ (ppm): 4.55 (m, 2H), 4.44 to 4.14 (m, 6H), 1.50 (s), 1.44 (s), (3H by combining 1.50 ppm and 1.44 ppm).

$^{19}$F-NMR (282.7 MHz, solvent: CDCl$_3$, standard: CFCl$_3$) δ (ppm): 43.5 (2F), −80.5 (1F), −81.8 (3F), −82.6 (3F), −85.3 (4F), −86.8 (1F), −111.7 (4F), −130.2 (2F), −132.5 (1F).

Example 4

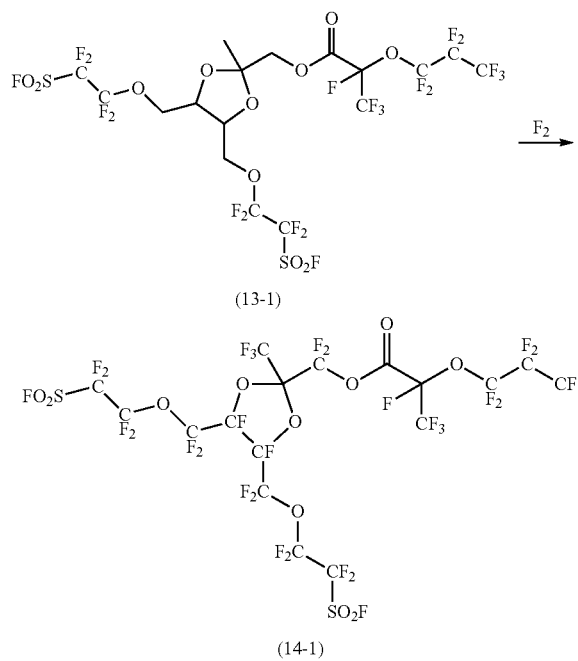

Into a stainless steel autoclave (inner volume: 3,000 mL), 4,200 g of CF$_3$CF$_2$CF$_2$OCF(CF$_3$)CF$_2$OCF(CF$_3$)COF (hereinafter referred to as an inactive fluid A) was introduced. As a transport device, a bellows pump having an ability of 300 L/Hr was used to circulate the inactive fluid A. By adjusting the amount of the refrigerant to flow through a heat exchanger provided in the middle of a circulation path, the temperature of the inactive fluid A in the autoclave was maintained at 20° C. A fluorine gas diluted to 25% with a nitrogen gas (hereinafter referred to as a 25% diluted fluorine gas) was continuously supplied from a stainless steel ejector provided in the pipe in a circulation path at a flow rate of 81.1 L/h. While maintaining the above conditions, the circulation was carried out for 1 hour.

Then, 300 g (0.29 mol) of the compound (13-1) was dissolved in R 113 (300 g), and the mixture was continuously supplied through a raw material supplying pipe provided in the middle of the circulation path with a flow amount of 56 g/h. Further, the inactive liquid containing a fluorinated compound was continuously withdrawn to make the volume of the liquid in the autoclave be approximately constant. As a result of subjecting the withdrawn crude liquid to a GC analysis, no presence of the compound (13-1) was confirmed in the inactive liquid.

The fluorinated product is an inactive liquid, and as the reaction proceeded, the circulating inactive fluid A was gradually replaced by the fluorinated product (compound (14-1)), whereby the circulating inactive fluid A was changed to a mixture of the inactive fluid A and the fluorinated product (compound (14-1)). Further, since the inactive fluid A and the fluorinated product (compound (14-1)) are the compounds having different boiling points, it is possible to easily separate them by distillation.

After supplying the entire solution of the compound (13-1), a 25% diluted fluorine gas was supplied for 48.5 hours. Further, only a nitrogen gas was blown in for 0.5 hour, and a crude liquid of the reaction was withdrawn. The total amount of the recovered crude liquid was 4,409 g. The obtained crude liquid was put in a flask, followed by heating and stirring under a reduced pressure, whereby it was possible to recover 331 g of a solution having the fluorinated product (compound (14-1)) as a main component (hereinafter referred to as a fluorinated crude liquid B).

Then, 230 g of the above fluorinated crude liquid B was dissolved in R113 (230 g), and the mixture was introduced in an autoclave (500 mL, made of nickel) followed by stirring, and it was maintained at 25° C. At the gas outlet of the autoclave, a condenser kept at 20° C., a NaF pellet-packed bed and a condenser kept at −10° C. were set in series. Further, a liquid-returning line was set to return the condensed liquid from the condenser kept at −10° C., to the autoclave. After a nitrogen gas was blown in for 1 hour, a fluorine gas diluted to 20% with a nitrogen gas (hereinafter referred to as 20% fluorine gas) was blown in at 11.4 NL/h.

Then, the temperature of the reaction solution was raised from 25° C. to 40° C., and with the 20% fluorine gas being blown in at the same constant flow rate into the autoclave, 9 ml of R 113 solution having a benzene concentration of 0.012 g/mL was injected, and the benzene injection inlet of the autoclave was closed, followed by stirring for 0.4 hour. 6 ml of the above benzene solution was injected, and the benzene injection inlet of the autoclave was closed, followed by stirring for 0.4 hour. Further, the same operation was repeated for 22 times. The total injected amount of benzene was 1.9 g and the total injected amount of R 113 was 153 ml.

Further, a nitrogen gas was blown in for 1 hour. When the object was quantified by $^{19}$F-NMR, formation of the compound (14-1) was confirmed, and as a result of the $^{19}$F-NMR analysis, it was confirmed that the compound was contained in a yield of 97%.

A reaction was carried out in the same manner with respect to the remaining fluorinated crude liquid B. Two of the reaction liquids were combined, and the solvent was distilled off to obtain 304 g of the compound (14-1).

$^{19}$F-NMR (282.7 MHz, solvent CDCl$_3$, standard: CFCl$_3$) δ (ppm): 45.5 (2F), −80.0 to −82.0 (18F), −84.6 to −87.5 (3F), −112.5 (4F), −113.0 to −123.0 (2F), −130.3 (2F), −132.1 (1F).

Example 5

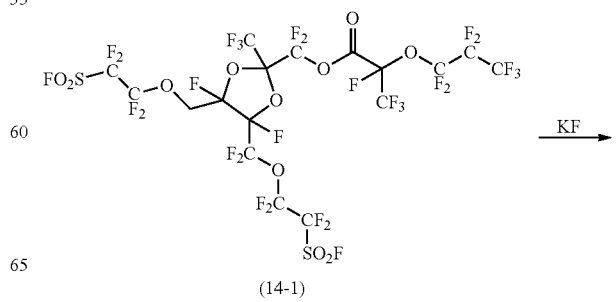

-continued

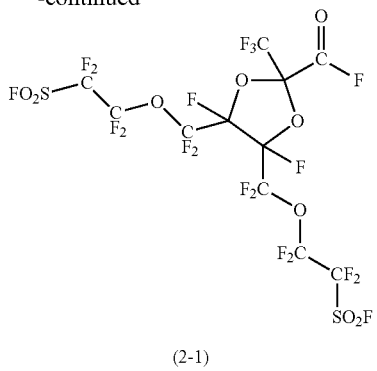

(2-1)

A stirring bar was put in a 500 mL 4-necked flask provided with a thermometer, and a distillation device was attached thereto. Under an atmosphere of nitrogen, 304 g of the compound (14-1) was introduced. Then, 3.36 g of KF (0.06 mol, "Chloro-catch F", manufactured by MORITA CHEMICAL INDUSTRIES, CO., LTD.) was added with stirring, followed by gradual heating in an oil bath. At the inner temperature of 87° C., $CF_3CF_2CF_2OCF(CF_3)COF$ started to be distilled. When the inner temperature reached 110° C. taking over a period of 2 hours, the inner temperature was kept at that level for 1 hour. Once it was cooled down, the distillation under a reduced pressure was carried out to obtain 176 g of a compound (2-1). The boiling point 117 to 144° C./0.67 to 0.80 kPa.

$^{19}$F-NMR (282.7 MHz, solvent $CDCl_3$, standard: $CFCl_3$) δ (ppm): 45.6 (2F), 27.2, 26.0, 25.0 (1F by combining 3 peaks), −80.1 to −81.8 (7F), −82.2 (4F), −112.5 (4F), −118.7, −119.4, −123.8, −129.4 (2F by combining 4 peaks).

Example 6

(2-1) → Δ → (3-1)

Into a tube reactor (made of inconel) having an inner diameter of 1.6 cm, glass beads (central particle size of from 105 to 125 μm, glass bead #150, manufactured by GAKUNAN KOHKI CO., LTD.) were filled until the filled height reached 40 cm, and then the tube reactor was heated to 325° C. While continuously heating the tube reactor, a gas mixture comprising 99 mol % of nitrogen gas and 1 mol % of vaporized gas of the compound (2-1) preliminary heated in the raw material line, was introduced from the bottom of the tube reactor in such a manner that the linear speed of the gas mixture in the tube reactor would be 2.65 cm/s. Further, at the top end of the tube reactor, a dry ice trap was set up. In such a state, the above gas mixture was supplied for 2 hours, and then only nitrogen gas was let flow through for 1 hour. The amount of the compound (2-1) introduced in the tube reactor was 3.96 g.

As a result of a GC analysis of the liquid (2.45 g) recovered in the dry ice trap, no raw material compound was confirmed, and the presence of the desired product having a purity of 85.5% was confirmed. The actual yield of the compound (3-1) was 60% taking into the consideration of the recovery rate of the above liquid. By distilling the heat-decomposition crude liquid obtained in the same manner, the objective compound (3-1) (a mixture of anti-form and syn-form) was obtained. The boiling point was from 99 to 102° C./0.40 to 0.53 kPa.

$^{19}$F-NMR of the anti-form (282.7 MHz, solvent $CDCl_3$, standard: $CFCl_3$) δ (ppm): 45.4 (2F), −81.6 (4F), −82.4 (4F), −112.6 (4F), −124.7 (2F), −128.2 (2F).

$^{19}$F-NMR of the syn-form (282.7 MHz, solvent $CDCl_3$, standard: $CFCl_3$) δ (ppm): 45.5 (2F), −81.8 (4F), −82.4 (4F), −112.6 (4F), −124.9 (2F), −127.3 (2F).

When the ratio between the anti-form and the syn-form was obtained from NMR, the ratio was such that anti-form:syn-form=3.3:1.0.

Example 7

Synthesis of Polymer

Into an autoclave (inner volume of 30 cm³, made of stainless steel), 1.33 g of the compound (3-1), 18.52 g of HCFC 225cb, 5.51 mg of methanol and 0.90 mg of peroyl IPP (diisopropyl peroxydicarbonate) were introduced, followed by cooling with liquid nitrogen and degassing. The inner temperature was increased to 40° C., and tetrafluoroethylene was introduced into the autoclave all at once at the initial stage. The pressure was adjusted to 0.49 MPa (gauge pressure). While maintaining the temperature to be constant, polymerization was carried out for 8 hours. The pressure at the completion of polymerization was 0.41 MPaG. The inside of the autoclave was cooled down to stop the polymerization, and the gas inside the system was purged.

After diluting the reaction liquid with HCFC 225cb, hexane was added, and a polymer was agglomerated and filtrated. After that, the polymer was stirred in HCFC 225cb, and it was reagglomerated by hexane. It was dried under reduced pressure over night at 80° C., to obtain 0.76 g of the polymer.

The content of monomer units of compound (3-1) obtained by fluorescent X-rays was 14.1 mol %, and the ion-exchange capacity was 1.58 meq/g. The molecular weight calculated as polystyrene, obtained by GPC was 1,100,000.

Example 8

Synthesis of Acid Type Polymer and Evaluation of Physical Property

The polymer obtained in Example 7 was subjected to press molding at 300° C. and was processed into a film (film thickness: approximately 100 μm). Then, into an aqueous solution containing 30 mass % of dimethylsulfoxide and 15 mass % of KOH, the polymer film was immersed at 80° C. for 16 hours, whereby a —SO$_2$F group in the polymer film was hydrolyzed and converted to a —SO$_3$K group.

Further, the polymer film was immersed in a 3 mol/L hydrochloric acid aqueous solution at 50° C. for 2 hours, and then the hydrochloric acid was changed. Such acid treatment was repeatedly carried out 4 times. It was sufficiently washed with deionized water, and a polymer film having a —SO$_3$K group in the polymer film converted to a —SO$_3$H group, was obtained.

The measurement of the softening temperature was carried out as follows. By using a dynamic viscoelasticity measuring device DVA200 (manufactured by ITK Co., Ltd.), the dynamic viscoelasticity of the above acid type film was carried out with a sample width of 0.5 cm, a length between chucks of 2 cm, a measuring frequency of 1 Hz and a rate of temperature increase of 2° C./min, and a temperature at which the elastic modulus became a half of the value at 50° C., was taken as a softening temperature. The softening temperature of the above acid type polymer was 117° C. Further, in the measurement of the dynamic viscoelasticity, the glass transition temperature (Tg) obtained from the peak value of tan δ was 158° C.

The specific resistance was measured by a known 4-terminal method and under a condition of constant temperature and humidity such as 80° C. and 95% RH with AC of 10 kHz and 1 V, wherein to a film having a width of 5 mm, a substrate having 4-terminal electrodes disposed every 5 mm was closely contacted. The specific resistance of the above acid type film was 2.2 Ω·cm.

Comparative Example

With respect to a film of a copolymer (ion exchange capacity: 1.10 meq/g, T$_Q$ 225° C.) of tetrafluoroethylene and CF$_2$=CFOCF$_2$CF(CF$_3$)OCF$_2$CF$_2$SO$_2$F converted to an acid-type, the physical properties were measured in the same manner as Example 8. The softening temperature and Tg were respectively 76° C. and 109° C. The specific resistance was 3.6 Ω/cm. Further, T$_Q$ value (unit: ° C.) of the above copolymer is an index for a molecular weight, and it is a temperature at which the extrusion amount would be 100 mm$^3$/sec when melt extrusion of a polymer is carried out by using a nozzle having a length of 1 mm and an inner diameter of 1 mm and under a condition of an extrusion pressure of 2.94 MPa. By using a flow tester CFT-500A (manufactured by Shimadzu Corporation), the extrusion amount was measured by changing the temperature, and the T$_Q$ value at which the extrusion amount became 100 mm$^3$/sec, was obtained.

The —SO$_2$F group-containing polymer obtained by polymerizing the compound of the present invention is useful for an application as a precursor of an electrolyte material. That is, by hydrolyzing a —SO$_2$F group of such a polymer, it is possible to obtain a polymer having a —SO$_3$H group, and the polymer having such a —SO$_3$H group is useful as an electrolyte material for e.g. brine electrolysis or a fuel cell. For example, such a polymer having a —SO$_3$H group can be used as an electrolyte for an ion-exchange membrane or in a catalyst layer for a polymer electrolyte fuel cell. Other than such an application, such a polymer having a —SO$_3$H group can be used for a material of various electrochemical processes as a solid electrolyte material. Further, the —SO$_2$F group-containing polymer itself is useful for an application as an optical material, etc.

The entire disclosure of Japanese Patent Application No. 2007-208024 filed on Aug. 9, 2007 including specification, claims and summary is incorporated herein by reference in its entirety.

What is claimed is:

1. A sulfonic acid group-containing polymer comprising one or more units of tetrafluoroethylene and at least one type of units represented by the following formula (5U):

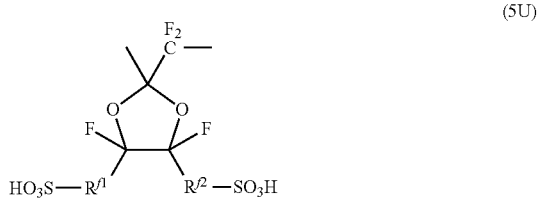

wherein each of R$^{f1}$ and R$^{f2}$ which are independent of each other, is a C$_{1-8}$ perfluoroalkylene group which may have an etheric oxygen atom between carbon atoms.

2. The sulfonic acid group-containing polymer according to claim 1, which has a molecular weight of from 5×10$^3$ to 5×10$^6$, and contains from 0.1 to 99.9 mol% of units represented by the formula (5U).

3. An electrolyte material for polymer electrolyte fuel cells, which to claim 1, s the sulfonic acid group-containing polymer according to claim 1.

* * * * *